United States Patent
Morrison et al.

(10) Patent No.: US 11,944,658 B2
(45) Date of Patent: Apr. 2, 2024

(54) METHODS OF HEAT INACTIVATION OF ADENOVIRUS

(71) Applicant: Ultragenyx Pharmaceutical Inc., Novato, CA (US)

(72) Inventors: Christopher J. Morrison, Arlington, MA (US); James D. Maratt, Belmont, MA (US)

(73) Assignee: Ultragenyx Pharmaceutical Inc., Novato, CA (US)

(*) Notice: Subject to any disclaimer, the term of this patent is extended or adjusted under 35 U.S.C. 154(b) by 284 days.

(21) Appl. No.: 17/238,743

(22) Filed: Apr. 23, 2021

(65) Prior Publication Data

US 2022/0072073 A1    Mar. 10, 2022

Related U.S. Application Data

(63) Continuation of application No. 16/085,177, filed as application No. PCT/US2017/024545 on Mar. 28, 2017, now Pat. No. 11,013,774.

(60) Provisional application No. 62/314,116, filed on Mar. 28, 2016.

(51) Int. Cl.
*A61K 35/761* (2015.01)
*C12N 7/00* (2006.01)
*C12N 15/85* (2006.01)
*C12N 15/86* (2006.01)

(52) U.S. Cl.
CPC .............. *A61K 35/761* (2013.01); *C12N 7/00* (2013.01); *C12N 15/85* (2013.01); *C12N 15/86* (2013.01); *C12N 2523/00* (2013.01); *C12N 2710/10361* (2013.01); *C12N 2750/14143* (2013.01); *C12N 2750/14151* (2013.01)

(58) Field of Classification Search
None
See application file for complete search history.

(56) References Cited

U.S. PATENT DOCUMENTS

| | | | |
|---|---|---|---|
| 5,387,484 A | 2/1995 | Doany et al. | |
| 5,658,785 A | 8/1997 | Johnson | |
| 5,688,676 A | 11/1997 | Zhou et al. | |
| 5,691,176 A | 11/1997 | Lebkowski et al. | |
| 5,741,683 A | 4/1998 | Zhou et al. | |
| 5,817,492 A | 10/1998 | Saito et al. | |
| 5,872,005 A | 2/1999 | Wang et al. | |
| 5,932,468 A | 8/1999 | Ristol Debart | |
| 6,004,797 A | 12/1999 | Colosi | |
| 6,127,175 A | 10/2000 | Vigne et al. | |
| 6,156,303 A | 12/2000 | Russell et al. | |
| 6,489,162 B1 | 12/2002 | Shenk et al. | |
| 6,566,118 B1 | 5/2003 | Atkinson et al. | |
| 6,723,551 B2 | 4/2004 | Kotin et al. | |
| 6,753,419 B1 | 6/2004 | Toniatti et al. | |
| 6,846,665 B1 | 1/2005 | Horer et al. | |
| 6,943,019 B2 | 9/2005 | Wilson et al. | |
| 7,271,002 B2 | 9/2007 | Kotin et al. | |
| 7,510,872 B2 | 3/2009 | Clark et al. | |
| 8,163,543 B2 | 4/2012 | Urabe et al. | |
| 8,409,842 B2 | 4/2013 | Clark et al. | |
| 8,512,981 B2 | 8/2013 | Hermens et al. | |
| 8,980,247 B2 | 3/2015 | Meyers et al. | |
| 2002/0081721 A1 | 6/2002 | Allen et al. | |
| 2002/0115189 A1 | 8/2002 | Natsoulis et al. | |
| 2002/0127582 A1 | 9/2002 | Atkinson et al. | |
| 2004/0235173 A1 | 11/2004 | Bleck et al. | |
| 2005/0112765 A1 | 5/2005 | Li et al. | |
| 2005/0148076 A1 | 7/2005 | Allen | |
| 2006/0013063 A1 | 1/2006 | Singh | |
| 2010/0248355 A1 | 9/2010 | Atkinson et al. | |
| 2011/0251547 A1 | 10/2011 | Xing et al. | |
| 2012/0058917 A1 | 3/2012 | Gaken et al. | |
| 2014/0056919 A1 | 2/2014 | Xing et al. | |
| 2014/0359799 A1 | 12/2014 | Wang et al. | |
| 2015/0024467 A1 | 1/2015 | Sheldon et al. | |
| 2015/0353899 A1 | 12/2015 | Pechan et al. | |

FOREIGN PATENT DOCUMENTS

| | | |
|---|---|---|
| WO | WO-1996/17947 A1 | 6/1996 |
| WO | WO-2000/09675 A1 | 2/2000 |
| WO | WO-2000/24916 A1 | 5/2000 |
| WO | WO-2000/47757 A1 | 8/2000 |
| WO | WO-2005/118792 A1 | 12/2005 |
| WO | WO-2010/148143 A1 | 12/2010 |

OTHER PUBLICATIONS

Clark et al., "Cell lines for the production of recombinant adeno-associated virus", Human Gene Therapy. vol. 6, (1995), pp. 1329-1341.

Conway et al., "High-titer recombinant adeno-associated virus production utilizing a recombinant herpes simplex virus type I vector expressing AAV-2 rep and cap", Gene Therapy. vol. 6, No. 6, (1999), pp. 986-993.

Cotmore et al., "Depletion of virion-associated divalent cations induces parvovirus minute virus of mice to eject its genome in a 3'-to-5' direction from an otherwise intact viral particle", Journal of Virology, American Society for Microbiology (ASM), vol. 84, No. 4, (2010), pp. 1945-1956.

Hermonat et al., "Human papillomavirus type 16 helper functions for adeno-associated virus type 2 replication", Molecular therapy. vol. 9,(2004), S289-290.

(Continued)

*Primary Examiner* — Robert M Kelly
(74) *Attorney, Agent, or Firm* — Goodwin Procter LLP

(57) ABSTRACT

The present disclosure generally relates to methods of protecting the genomic integrity and/or biological activity of AAV viral particles in a sample containing both AAV particles and helper virus particles during heat inactivation. The methods include heating, to a temperature greater than or equal to 45'C, a sample containing helper virus particles, AAV particles, and a buffer. The buffer includes a concentration of 10 mM or greater kosmotropic salts and/or a concentration of 10 mM or greater of divalent or trivalent cations.

20 Claims, 11 Drawing Sheets

(56) References Cited

OTHER PUBLICATIONS

Horowitz et al., "Biophysical and ultrastructural characterization of adeno-associated virus capsid uncoating and genome release", Journal of Virology 87.6, (2012): pp. 2994-3002.
Larkin. "Thermal Inactivation of Viruses," Technical Report, United States Army Natick Research and Development Command, Natick, MA, Food Sciences Laboratory, 1978, 1-48.
Liu et al., "Effect of magnesium ions on the thermal stability of human poly(A)-specific ribonuclease", FEBS Letters, Elsevier, , vol. 581, No. 5, (2007), pp. 1047-1052.
Lucas. "Viral Capsids and Envelopes: Structure and Function," Encyclopedia of Life Sciences (ELS) John Wiley & Sons, 2010, 1-7.
Martin et al., "Generation and Characterization of Adeno-Associated Virus Producer Cell Lines for Research and Preclinical Vector Production", Human Gene Therapy Methods. vol. 24, (2013), pp. 253-269.
Nakai et al., "Advances and Problems in the Gene Therapy for Hemophilia with Adeno-Associated Viral Vectors," Japanese Journal of Thrombosis and Hemostasis, vol. 14, No. 4, (2003), pp. 304-309.
Plummer et al., "Thermoinactivation of Herpes Simplex Virus and Cytomegalovirus," Journal of Bacteriology, vol. 89, No. 3, (1965), pp. 671-674.
Rayaprolu et al., "Comparative Analysis of Adeno-Associated Virus Capsid Stability and Dynamics", Journal of Virology., vol. 87, No. 24, (2013), pp. 13150-13160.
Strobel et al., "Comparative Analysis of Cesium Chloride- and Iodixanol-Based Purification of Recombinant Adeno-Associated Viral Vectors for Preclinical Applications", Human Gene Therapy Methods. vol. 26, No. 4, (2015), pp. 147-157).
Thorne et al., Characterizing clearance of helper adenovirus by a clinical rAAV1 manufacturing process. Biologicals, vol. 36, Issue 1, (2008), pp. 7-18.
Thorne et al., "Manufacturing recombinant adeno-associated viral vectors from producer cell clones", Human Gene Therapy. vol. 20, (2009), pp. 707-714.
Turnbull et al., "Adeno-Associated Virus Vectors Show Variable Dependence on Divalent Cations for Thermostability: Implications for Purification and Handling," Human Gene Therapy, 2004, 11(4): 629-635.
Virag et al., "Producing Recombinant Adeno-Associated Virus in Foster Cells: Overcoming Production Limitations Using a Baculovirus-Insect Cell Expression Strategy", Human Gene Therapy. vol. 20, No. 8 (2009), pp. 807-817.
Wang et al., "Identification of an adeno-associated virus binding epitope for AVB sepharose affinity resin", Molecular Therapy—Methods and Clinical Development. vol. 2, (2015), pp. 1-6.
Weitzman et al., "Adeno-associated virus biology", Adeno-Associated Virus: Methods and Protocols, Methods in Molecular Biology, vol. 807, (2011), pp. 1-23.
Wright et al., "Identification of factors that contribute to recombinant AAV2 particle aggregation and methods to prevent its occurrence during vector purification and formulation", Molecular Therapy, vol. 12, No. 1, (2005), pp. 171-178.
Wright, "Review: Transient Transfection Methods for Clinical Adeno-Associated Viral Vector Production", Human Gene Therapy. vol. 20, (2009), pp. 698-706.

A

B

C

D

METHODS OF HEAT INACTIVATION OF ADENOVIRUS

CROSS-REFERENCE TO RELATED APPLICATIONS

This application is a continuation application of U.S. patent application Ser. No. 16/085,177, filed on Sep. 14, 2018, which is a U.S. national stage application, filed under 35 U.S.C. § 371, of International Application No. PCT/US2017/024545 filed on Mar. 28, 2017, which claims priority to and the benefit of U.S. Provisional Application No. 62/314,116, filed on Mar. 28, 2016, and entitled "Methods Of Heat Inactivation Of Adenovirus," the entire disclosure of each of which are incorporated herein by reference in their entireties for all purposes.

BACKGROUND

Adeno-associated virus (AAV) is a non-pathogenic, replication-defective parvovirus. AAV vectors have many unique features that make them attractive as vectors for gene therapy. In particular, AAV vectors can deliver therapeutic genes to dividing and non-dividing cells, and these genes can persist for extended periods without integrating into the genome of the targeted cell. However, in order to produce AAV vectors, helper virus functions must be provided, sometimes in the form of an active infectious virus such as adenovirus (AV). During the AAV vector purification process to isolate the therapeutic AAV vectors, helper virus particles must be inactivated. However, common methods of helper virus inactivation, for example, heat inactivation, can also result in the destruction or degradation of the AAV vector genome, decreasing the quality and quantity of AAV vector that can be recovered from the inactivation process. This is particularly true for larger AAV vector genomes. There is therefore a need in the art to develop methods of protecting the integrity of AAV vectors during the heat inactivation of helper virus.

SUMMARY

This disclosure generally relates to methods of protecting the genomic integrity and/or biological activity of AAV viral particles in a sample containing both AAV particles and helper virus particles during heat inactivation. These methods generally permit the selective inactivation of helper virus particles by having an effect on helper virus particles that is greater than their effect on AAV particles. The methods include heating, to a temperature greater than or equal to 45° C., a sample containing helper virus particles, AAV particles, and a buffer. The buffer includes a concentration of 10 mM or greater kosmotropic salts and/or a concentration of 10 mM or greater of divalent or trivalent cations.

The methods include heating the sample to a temperature of greater than or equal to 45° C., greater than or equal to 46° C., greater than or equal to 47° C., greater than or equal to 48° C., greater than or equal to 49° C., greater than or equal to 50° C., or greater than or equal to 51° C. In certain embodiments the sample is heated to a temperature between 45° C. and 65° C., between 45° C. and 60° C., between 45° C. and 55° C., between 47° C. and 53° C., between 48° C. and 51° C., or between 48° C. and 50° C. For example, in certain embodiments the sample is heated to between 48° C. and 50° C., or to 48° C. or 49° C.

The period of time during which the sample is heated can vary. For example, in certain embodiments the sample is heated to the target temperature for a time period of between 1 minute and 6 hours, such as between 10 and 180 minutes, between 20 and 180 minutes, between 20 and 60 minutes, or between 20 and 40 minutes. Generally, higher temperatures or other conditions accelerating the inactivation of helper virus particles are used in conjunction with comparatively brief heating times, and vice versa.

In some methods a buffer containing a concentration of 10 mM or greater of divalent or trivalent metal cations is used. Exemplary cations include those of the following metals: Mg, Ca, Mn, Ni, Zn, Co, Sr, Cu, Cr, Fe, and Sc, which form cations such as $Mg^{2+}$, $Ca^{2+}$, $Mn^{2+}$, $Ni^{2+}$, $Zn^{2+}$, $Co^{2+}$, $Sr^{2+}$, $Cu^{2+}$, $Cr^{2+}$, and $Sc^{3+}$. In certain embodiments the buffer includes $Mg^{2+}$ and/or $Ca^{2+}$ at a concentration of 10 mM or greater.

In a subset of those buffers containing a concentration of 10 mM or greater of divalent or trivalent metal cations, the concentration is greater than 15 mM. For example, the concentration of cations may be greater than 20 mM, greater than 50 mM, greater than 100 mM, or greater than 200 mM. In another subset of buffers containing a concentration of mM or greater of divalent or trivalent metal cations, the concentration is from 10 mM and 500 mM. For example, the concentration of cations may be 20 mM to 400 mM, 30 mM to 300 mM, 50 mM to 250 mM, 70 mM to 200 mM, or at a concentration of 50 mM, 100 mM, 150 mM, or 200 mM.

In some methods a buffer with a concentration of 10 mM or greater of kosmotropic salts is used. Exemplary kosmotropic salts include ammonium sulfate, ammonium acetate, sodium citrate, sodium acetate, sodium sulfate, potassium phosphate, and cesium chloride, either separately or in any combination. If present, the kosmotropic salts are typically used at a concentration exceeding 10 mM, such as between 0.1 M and 1 M; between 0.2 M and 0.8 M; between 0.3 M and 0.7 M; between 0.4 M and 0.6 M; or 0.5 M.

In some methods, the buffer used contains a chaotropic salt. In a subset of buffers containing a chaotropic salt, the chaotropic salt is a salt of urea, or a salt of guanidine. In some methods, the buffer used contains a polyol. In a subset of buffers containing a polyol, the polyol is glycerol, propylene glycol, or 1,6-hexanediol.

In some methods, the buffer maintains pH over a range of temperatures between 4° C. and 70° C. A subset of buffers maintain pH between 3.0 and 10.0 at temperatures between 4° C. and 70° C. A further subset of these buffers maintains pH between 7.0 and 9.0 at temperatures between 4° C. and 70° C.

In some methods, the buffer is a tris buffer, a phosphate buffer, a triazolamine buffer, or a bis-tris propane buffer. In a subset of the tris and bis-tris propane buffers, the buffer comprises additional ingredients, including HEPES, citrate, NaCl, and Pluronic F68. In a subset of bis-tris propane buffers, the buffer comprises 40 mM bis-tris propane, 20 mM HEPES, 20 mM citrate, 200 mM NaCl, and 0.001% (w/v) Pluronic F68.

The methods disclosed herein are useful to preserve the genomic integrity of any AAV particle. In some methods AAV particle will comprise a genome of approximately 4.7 kb of DNA, of greater than 4.7 kb of DNA, of greater than 5.0 kb of DNA, or of approximately 5.1 kb of DNA. Alternatively, the AAV particle may comprise a genome of less than 4.0 kb of DNA, or of approximately 3.0 kb of DNA. The methods disclosed herein may be used with the AAV particles with genomes that are single-stranded or are substantially self-complementary.

Some methods of inactivation of the instant invention achieve a log reduction of active helper virus of greater than 5.0. A subset of these methods achieve a log reduction of helper virus of greater than 6.0, or of greater than 6.3. In some methods, the helper virus will be an adenovirus, a herpes virus, or a baculovirus. In a subset of the methods where the helper virus is an adenovirus, the adenovirus is Ad5.

BRIEF DESCRIPTION OF THE FIGURES

FIG. 2A depicts the results for a HEK293-produced, hu37 serotype, truncated product, FIG. 2B depicts the results for a HeLa-produced, hu37 serotype, oversized product, FIG. 2C depicts the results for a HEK293-produced, AAV8 serotype, single strand product, and FIG. 2D depicts the results for a HEK293-produced, AAV8 serotype, self-complementary product. A DNase-resistant particle qPCR (DRP-qPCR) assay was used to determine levels of AAV product pre- and post-exposure. Actual data points are shown by black dots, with the contour map interpolated between said data points.

FIG. 4A depicts the results for a HeLa-produced, hu37 serotype, oversized product, and FIG. 4B depicts the results for a HEK293-produced, hu37 serotype, oversized product. A DRP-qPCR assay was used to determine levels of AAV product pre- and post-exposure. Actual data points are shown by black dots, with the contour map interpolated between said data points.

FIG. 5A depicts the results for a background buffer of 40 mM bis-tris propane, 20 mM HEPES, 20 mM citrate, 200 mM NaCl, 0.001% (w/v) Pluronic F68, pH 8.0, FIG. 5B depicts the results for background buffer with 0.5 M Ammonium Sulfate added. A DRP-qPCR assay was used to determine levels of AAV product pre- and post-exposure. Actual data points are shown by black dots, with the contour map interpolated between said data points. A dotted line at 47° C. indicates the temperature where complete inactivation of Ad5 occurs (as determined in Example 1, see FIG. 1).

DETAILED DESCRIPTION

Figure 1:
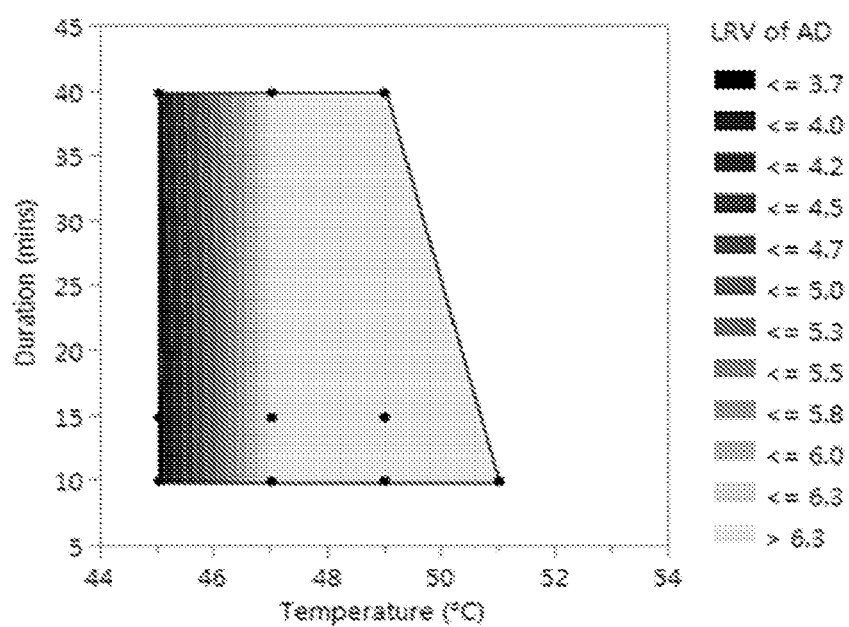
FIG. 1 depicts a contour plot showing the log reduction virus (LRV) of Ad5 as a function of temperature of exposure and time spent at temperature of exposure. An Ad5 infectivity assay was used to determine the level of inactivation of Ad5 particles. Actual data points are shown by black dots, with the contour map interpolated between said data points. The limit of quantitation of LRV in this assay was 6.3. Reduction of greater than 6.3 was not detectable.

Described herein are methods of inactivating helper virus, such as AV, in samples containing helper virus and AAV particles, resulting in increased recovery AAV particles with intact genomes and/or biological activity. The method comprises heating a sample containing helper virus and AAV particles and a buffer at sufficient temperature and for sufficient time to inactivate the helper virus particles. It has been unexpectedly shown that the addition of divalent or trivalent metal ions or kosmotropic salts to the buffer according to the instant invention results in increased recovery of AAV particles containing intact genomes.

Adeno-Associated Virus

AAV is a small, nonenveloped icosahedral virus of Dependoparvovirus genus of the family Parvovirus. AAV have a single-stranded linear DNA genome of approximately 4.7 kb. AAV includes numerous serologically distinguishable types including serotypes AAV-1 to AAV-12, as well as more than 100 serotypes from nonhuman primates. See, e.g., Srivastava, J. Cell Biochem., 105(1): 17-24 (2008); Gao et al., J. Virol., 78(12), 6381-6388 (2004). Any AAV type may be used in the methods of the present invention. AAV is capable of infecting both dividing and quiescent cells of several tissue types, with different AAV serotypes exhibiting different tissue tropism. AAV is non-autonomously replicating, and has a life cycle has a latent phase and an infectious phase. In the latent phase, after a cell is infected with an AAV, the AAV site-specifically integrates into the host's genome as a provirus. The infectious phase does not occur unless the cell is also infected with a helper virus (for example, AV or herpes simplex virus), which allows the AAV to replicate, and results in the production of both AAV and helper virus particles. This production of a mixed population of AAV particles and helper virus particles creates a significant problem if the AAV is to be used as a therapeutic vector, because the contaminating helper viruses must be removed or inactivated because of their potential pathogenicity and/or immunogenicity.

The wild-type AAV genome contains two 145 nucleotide inverted terminal repeats (ITRs), which contain signal sequences directing AAV replication, genome encapsidation and integration. In addition to the ITRs, three AAV promoters, p5, p19, and p40, drive expression of two open reading frames encoding rep and cap genes. Two rep promoters, coupled with differential splicing of the single AAV intron, result in the production of four rep proteins (Rep 78, Rep 68, Rep 52, and Rep 40) from the rep gene. Rep proteins are responsible for genomic replication. The Cap gene is expressed from the p40 promoter, and encodes three capsid proteins, VP1, VP2, and VP3, which are splice variants of the cap gene. These proteins form the capsid of the AAV particle.

Because the cis-acting signals for replication, encapsidation, and integration are contained within the ITRs, some or all of the 4.3 kb internal genome may be replaced with foreign DNA, for example, an expression cassette for an exogenous protein of interest. In this case the rep and cap proteins are provided in trans on, for example, a plasmid. In order to produce an AAV vector, a cell line permissive of AAV replication must express the rep and cap genes, the ITR-flanked expression cassette, and helper functions provided by a helper virus, for example AV genes Ela, E1b55K, E2a, E4orf6, and VA. (Weitzman et al., Adeno-associated virus biology. Adeno-Associated Virus: Methods and Protocols, pp. 1-23, 2011) Production of AAV vector can also result in the production of helper virus particles, which must be removed or inactivated prior to use of the AAV vector. Numerous cell types are suitable for producing AAV vectors, including HEK293 cells, COS cells, HeLa cells, Vero cells, as well as insect cells (see e.g. U.S. Pat. Nos. 6,156,303, 5,387,484, 5,741,683, 5,691,176, 5,688,676, 8,163,543, US 20020081721, WO 00/47757, WO 00/24916, and WO 96/17947). AAV vectors are typically produced in these cell types by one plasmid containing the ITR-flanked expression cassette, and one or more additional plasmids providing the additional AAV and helper virus genes.

AAV vectors of any serotype may be used in the present invention. Similarly, it is contemplated that and AV type may be used, and a person of skill in the art will be able to identify AAV and AV types suitable for the production of their desired AAV vector. AAV and AV particles may be minimally purified, for example by affinity chromatography, iodixonal gradient, or CsCl gradient. Samples containing AAV and AV particles that have been further purified may also be used in the methods of the present invention, as are samples that have been less purified.

The genome of wild-type AAV is single-stranded DNA and is 4.7 kb. AAV vectors may have single-stranded genomes that are 4.7 kb in size, or are larger or smaller than 4.7 kb, including oversized genomes that are as large as 5.2 kb, or as small as 3.0 kb. Further, vector genomes may be substantially self-complementary, so that within the virus the genome is substantially double stranded. As has been shown here, AAV vectors with oversized genomes are at increased susceptibility to heat degradation. Therefore, AAV vectors with oversized genomes are preferred for use in the method of the instant invention. However, it will be understood by those of skill in the art that increasing the stability of all types of AAV vectors during heat inactivation is valuable because it allows for increasingly stringent inactivation conditions. Therefore, AAV vectors containing genomes of all types are suitable for use in the method of the instant invention.

Helper Virus

As discussed above, AAV requires co-infection with a helper virus in order to enter the infectious phase of its life cycle. Helper viruses include Adenovirus (AV), and herpes simplex virus (HSV), and systems exist for producing AAV in insect cells using baculovirus. It has also been proposed that papilloma viruses may also provide a helper function for AAV. See, Hermonat et al., Molecular Therapy 9, S289-S290 (2004). Helper viruses include any virus capable of creating an allowing AAV replication. Any helper virus may be used in the current invention, provided that it exhibits a lower thermal stability than AAV. AV is a nonenveloped nuclear DNA virus with a double-stranded DNA genome of approximately 36 kb. AV is capable of rescuing latent AAV provirus in a cell, by providing E1a, E1b55K, E2a, E4orf6, and VA genes, allowing AAV replication and encapsidation.

HSV is a family of viruses that have a relatively large double-stranded linear DNA genome encapsidated in an icosahedral capsid, which is wrapped in a lipid bilayer envelope. HSV are infectious and highly transmissible. The following HSV-1 replication proteins were identified as necessary for AAV replication: the helicase/primase complex (UL5, UL8, and UL52) and the DNA binding protein ICP8 encoded by the UL29 gene, with other proteins enhancing the helper function.

Other helper viruses, such as baculovirus, may be used with the present invention, provided that they are capable of supporting AAV replication, either naturally or in a modified form, and that they exhibit a lower level of thermal stability than AAV.

Production of AAV Vector

AAV vectors may be produced in mammalian or insect cells by many methods known in the art. Any method of production will be suitable to produce starting material for the present invention provided that the result of the production method is a sample containing both AAV and helper virus. The manufacturing process includes providing the cells with a plasmid that contains the AAV vector genome, with AAV rep and cap gene functions as well as additional helper functions. Additional helper functions can be provided by for example, an AV infection, by a plasmid that carries all of the required AV helper function genes, or by other viruses such as HSV or baculovirus. AAV production methods suitable for use with the methods of the current invention include those disclosed in Clark et al., Human Gene Therapy 6:1329-1341 (1995); Martin et al., Human Gene Therapy Methods 24:253-269 (2013); Thorne et al., Human Gene Therapy 20:707-714 (2009); Fraser Wright, Human Gene Therapy 20:698-706 (2009); Virag et al., Human Gene Therapy 20:807-817 (2009).

The AAV product is harvested from a cell lysate or from the cell culture media. Primary purification steps include affinity and ion-exchange chromatography to remove cell contaminants. The purified sample is filtered and stored at ≤−60° C.

Cell Lysis

AAV particles may be obtained from infected cells by lysing the cells. Lysis of AAV-infected cells can be accomplished by methods that chemically or enzymatically treat the cells in order to release infections viral particles. These methods include the use of nucleases such as benzonase or DNAse, proteases such as trypsin, or detergents or surfactants. Physical disruption, such as homogenization or grinding, or the application of pressure via a microfluidizer pressure cell, or freeze-thaw cycles may also be used. Alternatively, supernatant may be collected from AAV-infected cells without the need for cell lysis.

Purification of Viral Particles

Prior to the inactivation methods of the current invention, it may be necessary to purify the sample containing AAV and helpervirus particles to remove, for example, the cellular debris resulting from cell lysis. Methods of minimal purification of helper virus and AAV particles are known in the art, and any appropriate method can be used to prepare samples containing both AAV and helper virus particles for use in the methods of the present invention. Two exemplary purification methods are Cesium chloride (CsCl)— and iodixanol-based density gradient purification. Both methods are described in Strobel et al., Human Gene Therapy Methods., 26(4): 147-157 (2015). Minimal purification can also be accomplished using affinity chromatography using, for example AVB Sepharose affinity resin (GE Healthcare Bio-Sciences AB, Uppsala, Sweden). Methods of AAV purification using AVB Sepharose affinity resin are described in, for example, Wang et al., Mol Ther Methods Clin Dev., 2:15040 (2015).

Heat Inactivation

Heat inactivation techniques are based on the different thermal stabilities of AAV and helper virus particles. For example, AAV particles can be heated to temperatures as high as 56° C. and still remain intact, while AV particles are rendered inactive. Conway et al., Gene Therapy 6, 986-993, 1999, describes differential heat inactivation of HSV in AAV containing samples. Heat inactivation may be accomplished by any known methodology. In the examples described below, heat inactivation was accomplished using a thermocycler to rapidly heat and cool sample volumes of 300 μL or less. This system was chosen because it relies on heat transfer that is primarily conductive, making it a viable model for both continuous-flow systems and for larger batch systems that employ active mixing. Examples of continuous-flow systems include passage of the sample through a continuous-flow heat exchanger, such as the DHX™ Single-Use Heat Exchanger for Bio-therapeutic Manufacturing (Thermo Fisher Scientific, Millersburg, PA). Such systems allow the operator to control the heat inactivation process by controlling the flow rate of the sample through the heat exchanger, thus controlling the duration of the heating process, and the temperature of the heat exchanger, thus controlling the temperature of heat inactivation.

Alternatively heat inactivation may be accomplished using batch systems of various sizes. For example, heat inactivation may be accomplished at the 1 L scale, by placing the AAV containing sample in a 1 L PETG bottle and placing the bottle in a water bath set at the desired inactivating temperature for the desired period of time, with mixing, for example, the samples may be heated to 47° C. for 20 minutes. At a larger scale, heat inactivation may be accomplished by placing the AAV containing sample in a 5 L bioprocessing bag on a temperature controlled rocking platform set at the desired inactivating temperature, for the desired period of time. For example, the rocking platform may be set to 49° C. at a rocking speed of 30 RPM, with a 12° angle of mixing for 40 minutes.

Heat inactivation may occur at any temperature where there is a sufficient difference in stability between AAV particles and helper virus particles that helper virus particles are substantially inactivated while active AAV particles remain. In the current invention, samples containing AAV and helper virus particles are heated to a temperature of greater than or equal to 45° C., and generally to a temperature of between 45° C. and 55° C., with temperatures of 49° C.±2° C. being most often used. The sample is generally held at temperature for a period of from 1 to 60 minutes, with 10 to 40 minutes being most often used. However, as shown in FIG. 1, heat inactivation is largely independent of time, so the duration of the heating step will be a function of the time necessary to bring the entire sample to temperature. For example, a 300 μL sample size may be brought to a uniform temperature within seconds, while a multi-liter tank may many minutes to reach a uniform temperature. Further, a person of skill in the art will understand that higher temperatures may be required to achieve greater levels of AV reduction.

Measuring Inactivation Efficacy

Once heat inactivation has been accomplished, it may be necessary or desirable to determine the efficiency of inactivation. The efficacy of an inactivation protocol is determined by assays that detect the presence of replication competent helper virus, such as a plaque assay. Plaque assays for helper virus are well known to those in the art, including plaque assays for AV, HSV, baculovirus, and others. Plaque assays of adenovirus may be conducted using any appropriate cell type, for example HeLa or HEK293 cells. Standard plaque assay protocols are described in, for example, Current Protocols in Human Genetics, 2003. Alternative assays for measuring adenoviral titers include those that allow the identification of infected cells in culture by detecting viral proteins, such as hexon proteins, using immunocytochemical staining. Such assays include the QuickTiter™ Adenovirus Titer Immunoassay Kit (Cell Biolabs, San Diego, CA). The efficiency of inactivation is generally reported as the log reduction of virus (LRV).

Quantification of AAV Particles

Quantification of AAV particles is complicated by the fact that AAV infection does not result in cytopathic effect in vitro, and therefore plaque assays cannot be used to determine infectious titers. AAV particles can be quantified using a number of methods, however, including quantitative polymerase chain reaction (qPCR) (Clark et al., Hum. Gene Ther. 10, 1031-1039 (1999)) or dot-blot hybridization (Samulski et al., J. Virol. 63, 3822-3828 (1989)), or by optical density of highly purified vector preparations (Sommer et al., Mol. Ther. 7, 122-128 (2003)). DNase-resistant particles (DRP) can be quantified by real-time quantitative polymerase chain reaction (qPCR) (DRP-qPCR) in a thermocycler (for example, a iCycler iQ 96-well block format thermocycler (Bio-Rad, Hercules, CA)). Samples containing AAV particles are incubated in the presence of DNase I (100 U/ml; Promega, Madison, WI) at 37° C. for 60 min, followed by proteinase K (Invitrogen, Carlsbad, CA) digestion (10 U/ml) at for 60 min, and then denatured at 95° C. for 30 min. The primer—probe set used should be specific to a non-native portion of the AAV vector genome, for example, the poly(A) sequence of the protein of interest. The PCR product can be amplified using any appropriate set of cycling parameters, based on the length and composition of the primers, probe, and amplified sequence. Alternative protocols are disclosed in, for example, Lock et al., Human Gene Therapy Methods 25(2): 115-125 (2014).

The infectivity of AAV particles can be determined using a $TCID_{50}$ (tissue culture infectious dose at 50%) assay, as described for example in Zhen et al., Human Gene Therapy 15:709-715 (2004). In this assay, AAV vector particles are serially diluted and used to co-infect a Rep/Cap-expressing cell line along with AV particles in 96-well plates. 48 hours post-infection, total cellular DNA from infected and control wells is extracted. AAV vector replication is then measured using qPCR with transgene-specific probe and primers. $TCID_{50}$ infectivity per milliliter ($TCID_{50}$/ml) is calculated with the Kärber equation, using the ratios of wells positive for AAV at 10-fold serial dilutions.

Background Buffer

The methods of the present invention include the use of a background buffer. Background buffer can be any buffer capable of maintaining a stable pH over a broad temperature range, for example, maintaining pH in a range of 3.0 to 10.0 when the buffer changes temperature from 4° C. and 70° C. The buffer may also maintain a pH of between 7.0 and 9.0 when the buffer changes temperature from 4° C. and 70° C. Exemplary background buffers include systems buffered by glycine, citrate, succinate, acetate, MES (2-(N-morpholino) ethanesulfonic acid), bis-tris (bis-(2-hydroxyethyl)-imino-tris-(hydroxy methyl)-methane), phosphate, pipes (1,4-piperazinediethanesulfonic acid), mopso (3-morpholino-2-hydroxypropanesulfonic acid), BTP (1,3-bis(tris(hydroxymethyl)methylamino)propane), MOPS (3-morpholinopropane-1-sulfonic acid), TES 2-[[1,3-dihydroxy-2-(hydroxymethyl)propan-2-yl]amino]ethanesulfonic acid, HEPES (4-(2-hydroxyethyl)-1-piperazineethanesulfonic acid), TEA (tris base, acetic acid, and EDTA), tris, tricine, bicine, lactate, formate, and MMA (2-methylpropanedioic acid). One exemplary background buffer includes: 40 mM bis-tris propane, 20 mM HEPES, 20 mM citrate, 200 mM NaCl, and 0.001% (w/v) Pluronic F68, and is at pH 8.0 at room temperature.

Di- and Trivalent Metal Ions

A subset of the buffers used in the present invention contain or more divalent or trivalent metal cations, for example $Mg^{2+}$, $Ca^{2+}$, $Mn^{2+}$, $Ni^{2+}$, $Zn^{2+}$, $Co^{2+}$, $Sr_{2+}$, $Cu^{2+}$, $Cr^{2+}$, and $Sc^{3+}$. Salts of the aforementioned cations may also be employed. When employed in the present invention, di- or trivalent cations are present at a total concentration of greater than mM. As shown in the Examples below, all buffers containing more than 10 mM di- or trivalent cations that were tested provided significant protection relative to samples heated in control buffer. The highest levels of protection were observed in buffers containing 50 mM to 200 mM $MgCl_2$. For metal ions that are highly soluble, such as cations of Ca or Mg, it will be understood by those of skill in the art that increasing the concentration of the cation beyond the amount needed to achieve maximal protection of AAV will not have negative effects on AAV protection and will produce equivalent results. The buffer of the present invention may also include chaotropic salts, including salts of urea or guanidine. The buffer may also include a polyol, preferred polyols being glycerol, propylene glycol, and 1,6-hexanediol.

Kosmotropic Salts

A subset of the buffers used in the present invention contain kosmotropic salts. Kosmotropic salts are co-solvents that contribute to the stability and structure of water-water interactions. Kosmotropic salts also stabilize proteins, membranes, and hydrophobic aggregates in solution. In one embodiment of the present invention, the buffer includes one or more kosmotropic salts, particularly a strong kosmotropic salts such as ammonium sulfate, ammonium acetate, sodium citrate, sodium acetate, sodium sulfate, potassium phosphate, and cesium chloride. Kosmotropic salts are useful in the present invention at a concentration of greater than 10 mM, for example, at a concentration of 0.1 M to 1 M, of 0.2 M to 0.8 M, of 0.3 M to 0.7 M, of 0.4 M to 0.6 M, or of 0.5 M.

EXAMPLES

The examples which follow are intended in no way to limit the scope of this invention but are provided to illustrate aspects of the disclosed methods. Many other embodiments of this invention will be apparent to one skilled in the art.

Example 1

Ad5 AV particles were produced using standard techniques, and minimally purified via CsCl gradient. Ad5 particles were dialyzed into background buffer (40 mM bis-tris propane, 20 mM HEPES, 20 mM citrate, 200 mM NaCl, 0.001% (w/v) Pluronic F68, pH 8.0). Heating was conducted using a thermocycler to immediately heat a sample to a desired temperature, hold at the desired temperature, and then immediately cool the samples. Samples of Ad5 particles in buffer were contained in polypropylene tubes and were of 300 µL or lower in volume. Ad5 AV samples were heated to 45° C., 47° C., 49° C., or 51° C., for a duration of either 10 minutes, 15 minutes, or 40 minutes, with the exception of Ad5 AV samples heated to 51° C., which were only held at that temperature for 10 minutes. Following heat treatment, Ad5 infectivity was then measured using the QuickTiter™ Adenovirus Titer Immunoassay Kit (Cell Biolabs, San Diego, CA) according to the manufacturer's instructions.

Ad5 AV heat inactivation data is shown in FIG. 1 as log reduction virus (LRV) of the Ad5 virus, with a >6 LRV being desired. As can be seen in FIG. 1, the inactivation of the Ad5 material is highly temperature dependent, with time at temperature not having a gross impact on inactivation. Based upon these data, it is desirable to carry out the inactivation step at 47° C. or higher in temperature.

Example 2

AAV vectors of different serotypes and containing different genome types and sizes were tested for the effect of AV heat inactivation protocols on AAV genomic stability. Two serotypes were tested, AAV8 and hu37, with three different genomes. The following AAV vectors were tested:

(A) hu37 capsid containing a single-stranded construct (4.7 kb)
(B) hu37 capsid containing an oversized single-stranded construct (5.1 kb)

(C) AAV8 capsid containing a small single-stranded construct (4.1 kb)

(D) AAV8 capsid containing a self-complementary construct (4.6 kb)

AAV vectors (A) (C) and (D) were produced in HEK293cells, particle (B) was produced in HeLa cells. All vectors were minimally purified via affinity chromatography or iodixonal gradient using standard techniques. Vectors were dialyzed into background buffer (40 mM bis-tris propane, 20 mM HEPES, 20 mM citrate, 200 mM NaCl, 0.001% (w/v) Pluronic F68, pH 8.0). Heating was conducted using a thermocycler to immediately heat a vector sample to a desired temperature, hold at the desired temperature, and then immediately cool the samples. Vector samples were contained in polypropylene tubes and were of 300 μL or lower in volume. Vector samples were exposed to heat inactivation conditions as follows: Vectors (A), (B), and (C) were heated to 45° C., 47° C., or 49° C., vector (B) was heated to 45° C., 47° C., 49° C., 51° C., or 53° C. All vectors were tested after heating for 10, 20, or 40 minutes. Post heat treatment samples were analyzed for genome stability by DRP-qPCR assay.

Figure 2:
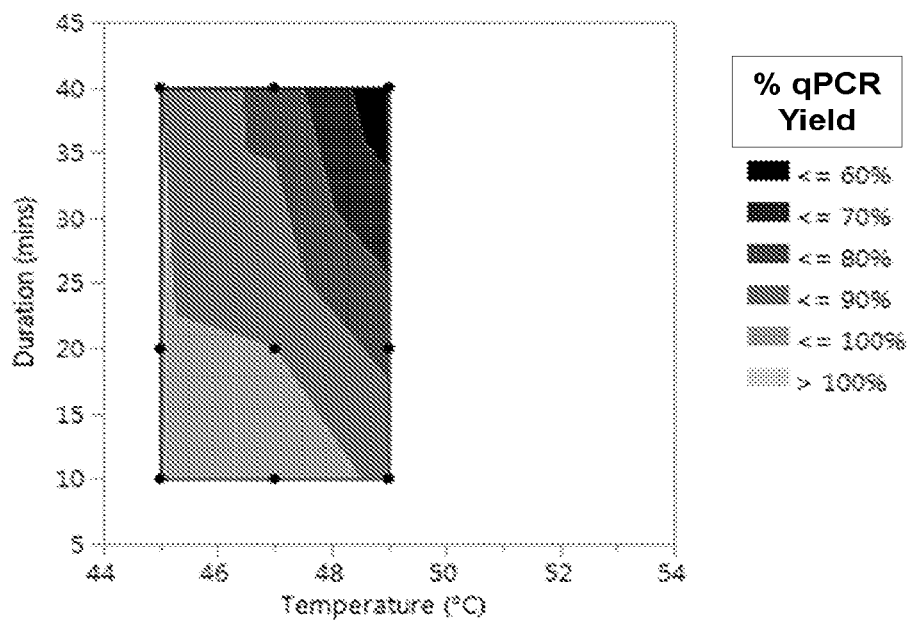
FIG. 2 depicts contour plots showing the percent yield of various AAV products as a function of temperature of exposure and time spent at temperature of exposure.
Figure 2:
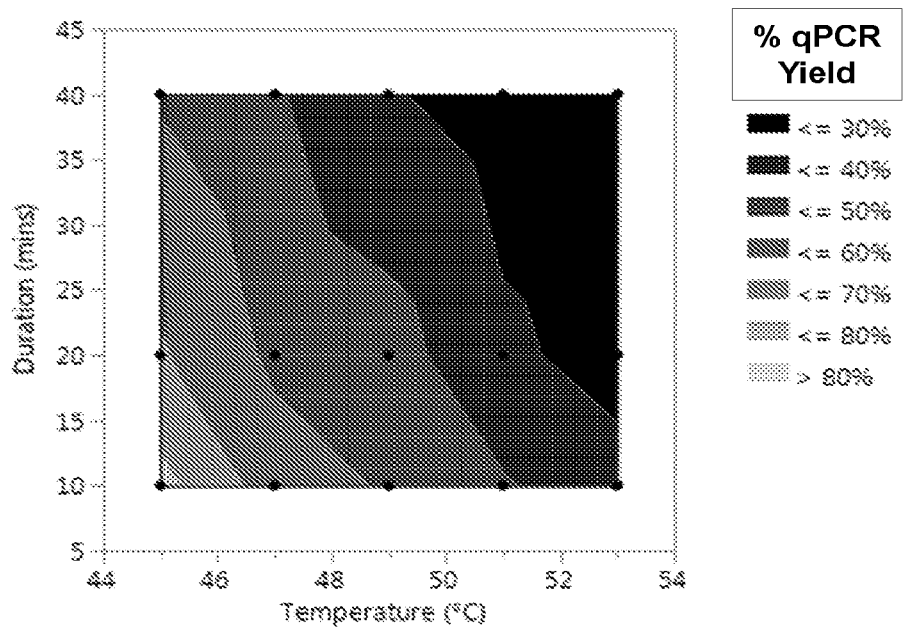
Figure 2:
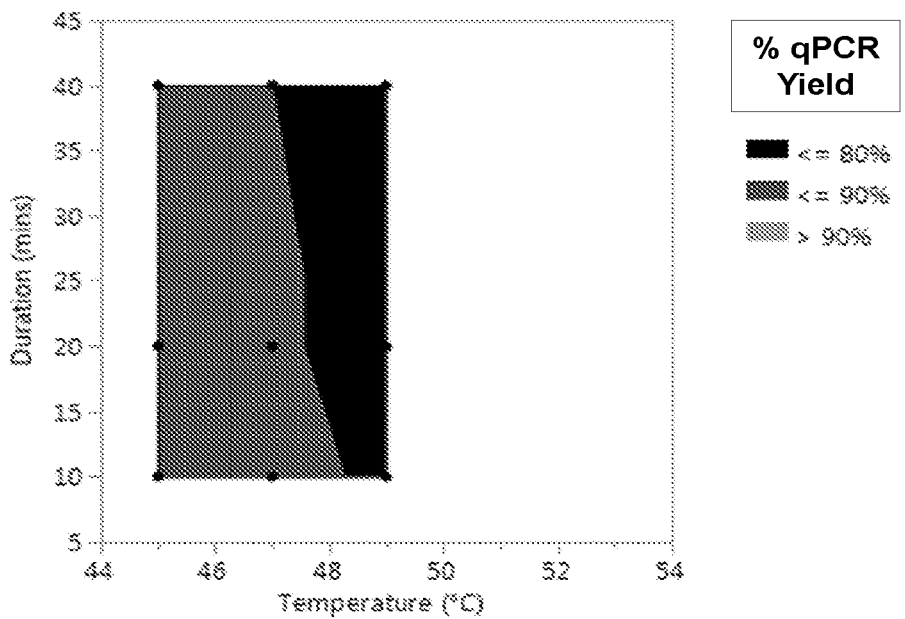
Figure 2:
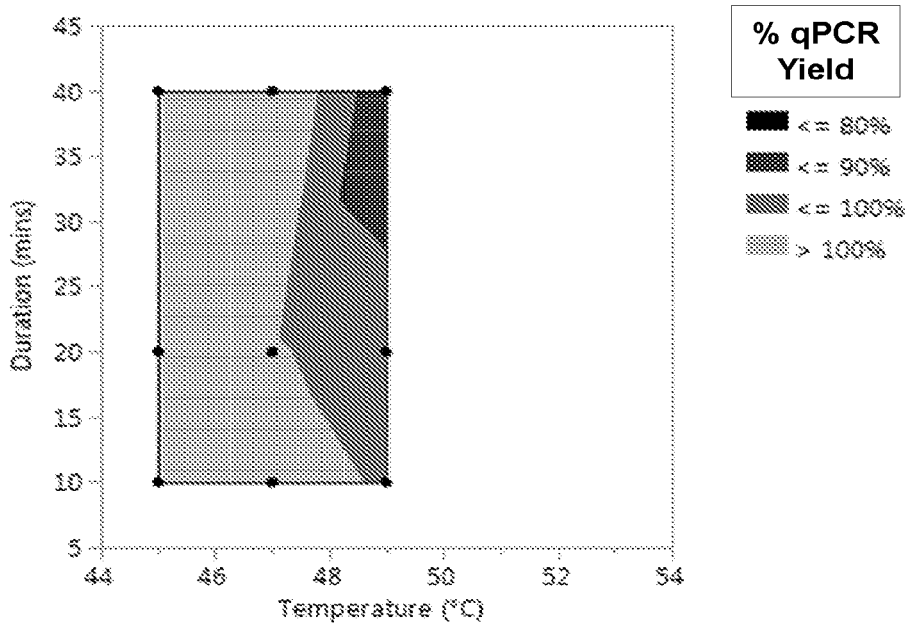

Data from this experiment are shown in FIG. 2. The genomic degradation of the AAV product following inactivation protocols was determined by DRP-qPCR assay and represented as % qPCR yield. Percent qPCR yield was determined by comparing against a starting sample which was not exposed to elevated temperatures and kept at 4° C. As can be seen in the figure, for serotype AAV8 with a single strand or self-complementary construct of <4.7 kb in length (FIG. 2C and FIG. 2D respectively), the elevated temperatures and time at temperature did not significantly degrade the AAV material. In contrast, the hu37 serotype with a single strand construct (4.7 kb) was more sensitive to heat and time at heat in comparison to a similar sized construct produced in AAV8 (FIG. 2A vs. FIG. 2C). Finally, for the hu37 serotype, an oversized construct (5.1 kb) had a significantly negative impact on stability against heat when compared to a construct of normal genome size (4.7 kb) (FIG. 2B vs FIG. 2A). These results indicate that different serotypes have different heat stability profiles, but more importantly, that construct size has a significant impact heat on the stability of the capsid.

Example 3

Two methods of determining the genome integrity of AAV vectors were compared. Samples of hu37 vector containing an oversized genome (5.1 kb) were heated to 22° C., 45° C., 47° C., 49° C., 51° C., or 53° C. for 20 minutes, and recovery was measured either by DRP-qPCR assay or by a $TCID_{50}$ infectivity assay. Control samples were kept frozen until genome integrity measurements were made.

Figure 3:
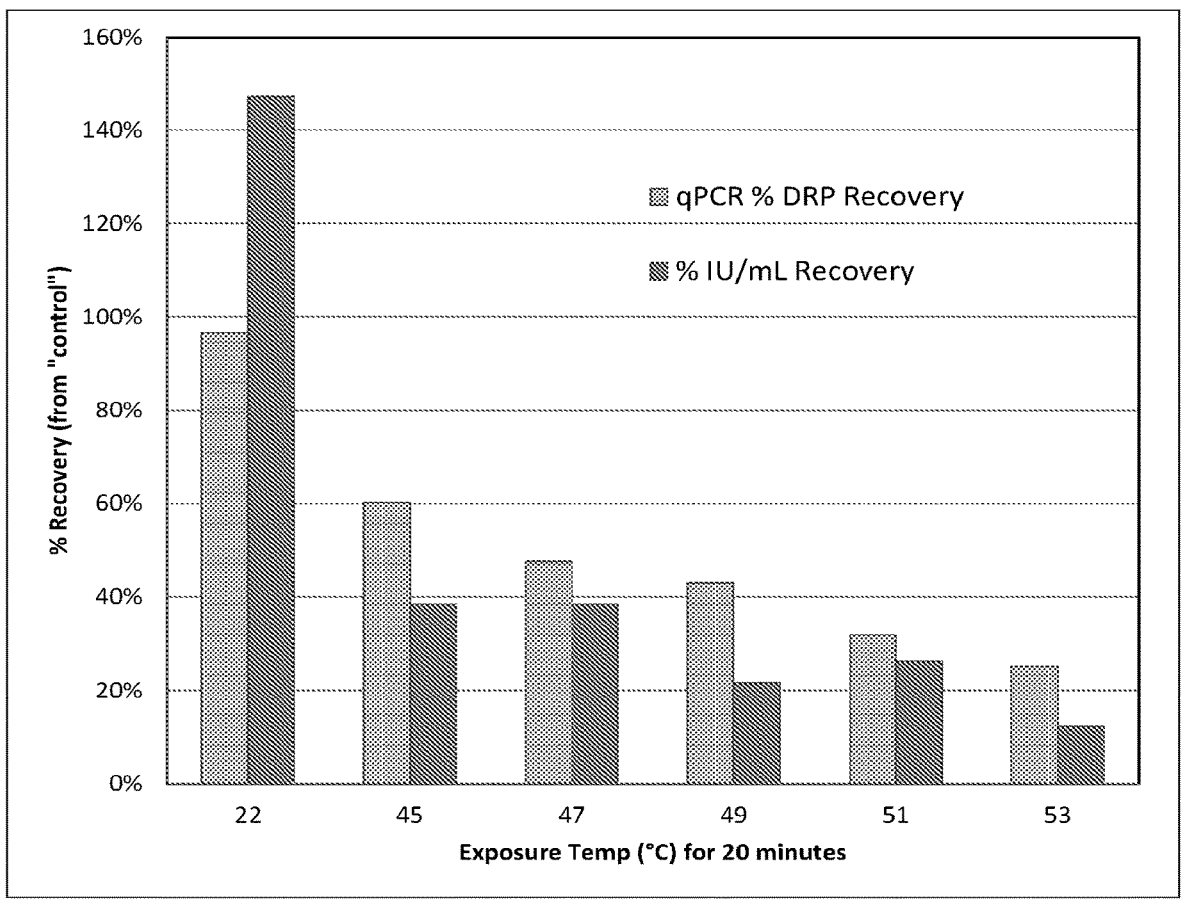
FIG. 3 depicts a comparison of percent recovery results as determined using a DRP-qPCR assay (dark bars) and a TCID50 infectivity assay (light bars). Samples tested were the same as shown in FIG. 2B for the 20 minute exposure time. The "control" was a load sample which remained frozen for the entire experiment.

FIG. 3 presents a comparison of data collected using DRP-qPCR versus the $TCID_{50}$ infectivity assay. As can be seen in the figure, the resulting recoveries by the two techniques gave qualitatively similar results, and gave the same trend in decreasing capsid quality with increasing temperature. These data reinforce the use of the DRP-qPCR assay as a model by which to carry out preliminary investigations looking to mitigate capsid degradation when exposed to elevated temperatures.

Example 4

Figure 4:
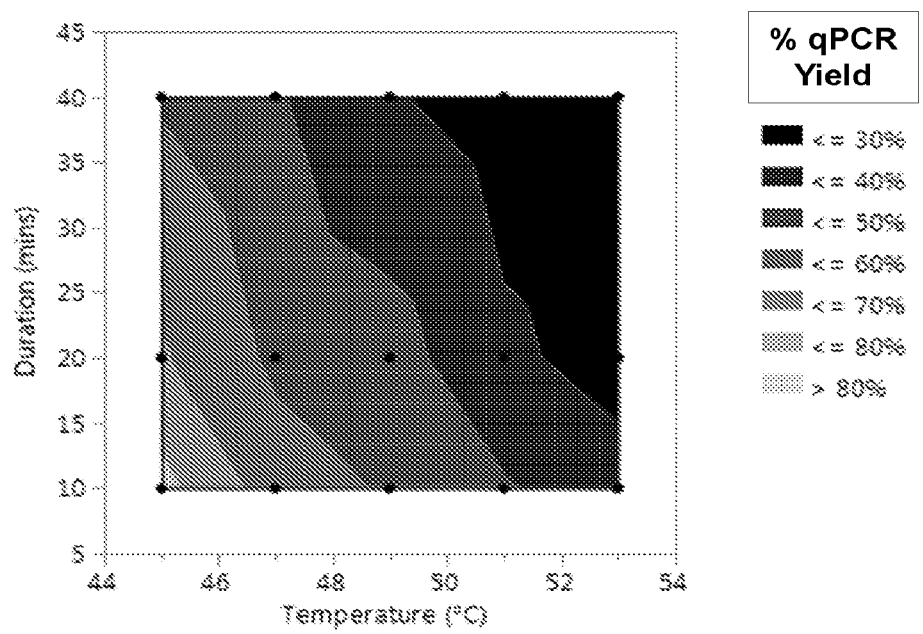
FIG. 4 depicts a contour plot showing the percent yield of two AAV products as a function of temperature of exposure and time spent at temperature of exposure.
Figure 4:
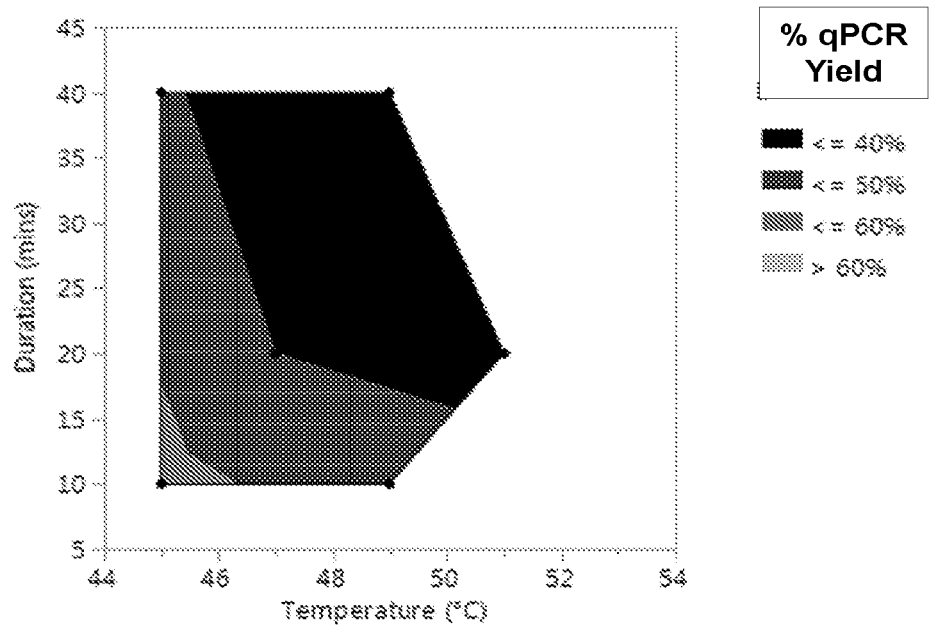

The effect of the cellular production system on heat sensitivity was tested by comparing the heat stability of AAV vectors produced using different cell types. Vectors of serotype hu37, containing an oversized genome (5.1 kb) were produced using either HeLa cells or HEK293 cells. Vector samples were heated to 45° C., 47° C., 49° C., 51° C., or 53° C. for 10, 20, or 40 min. Genomic integrity was measured by DRP-qPCR. As shown in FIG. 4, not all data points were repeated for both vector types. However, results from the two experiments were qualitatively similar. These data suggest that the cell line production system used to create the AAV material did not have a significant impact on the heat stability of the resulting AAV. In addition, these data support the overall finding that the hu37 serotype, containing an oversized construct material is highly sensitive to heating conditions required for Ad5 inactivation (as shown in FIG. 1).

Example 5

AAV vector samples of hu37 serotype containing an oversized genome were produced as described in Example 2. Samples were dialyzed into either (A) standard background buffer (40 mM bis-tris propane, 20 mM HEPES, 20 mM citrate, 200 mM NaCl, (w/v) Pluronic F68, pH 8.0) or (B) standard background buffer containing 0.5 M ammonium sulfate. Samples were heated as follows: 45° C. for 10 and 40 minutes, 47° C. for minutes, 49° C. for 10 minutes and 40 minutes, and 51° C. for 20 minutes. Genomic integrity was measured by DRP-qPCR.

Figure 5:
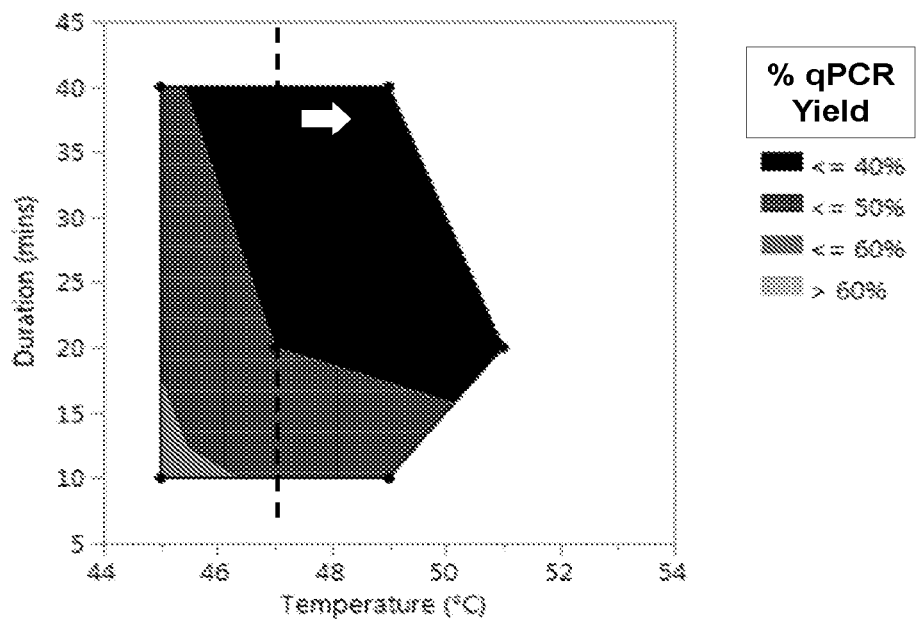
FIG. 5 depicts a contour plot showing the percent yield of HEK293-produced, hu37 serotype, oversized product in different background buffers as a function of temperature of exposure and time spent at temperature of exposure.
Figure 5:
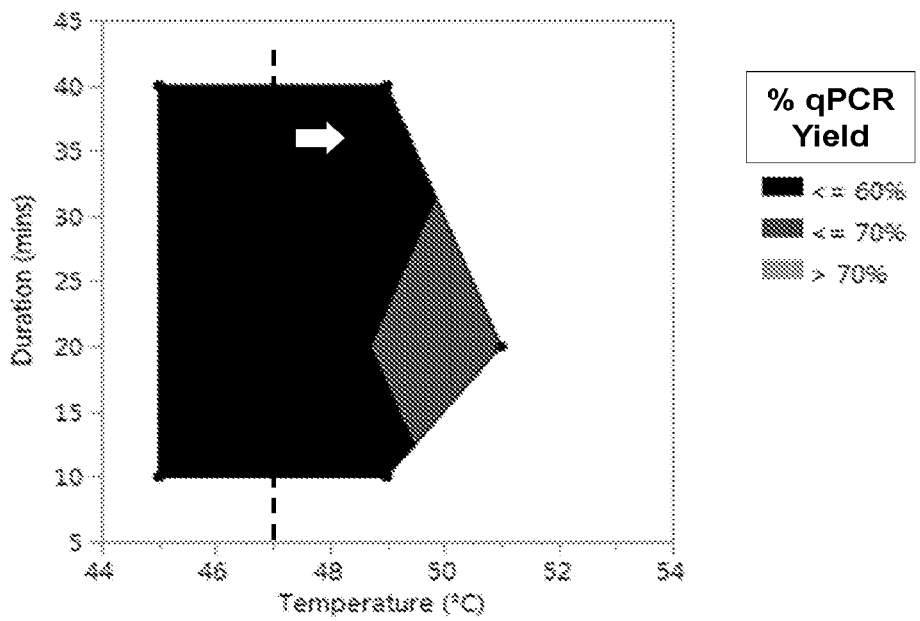

As show in FIG. 5, by adding 0.5 M ammonium sulfate to the background buffer the heat stability of the AAV vector was improved (FIG. 5A vs. FIG. 5B). These data show that by adding strong kosmotropic salts to the buffer formulation used during the heat inactivation step, the AAV vector may be protected for the degrading impact of the elevated temperatures.

These data demonstrate that AAV can be sensitive to conditions required for the heat inactivation of Ad5 virus. Stability of the AAV appears to be serotype dependent, and the use of oversized constructs (oversized being defined as a construct of 4.7 kb length or larger) can have a significantly detrimental impact on the stability of the AAV material. Data shown in this report also suggest that the addition of kosmotropic salts can have a beneficial impact, increasing the stability of the AAV material when exposed to elevated temperatures.

Example 6

AAV vector samples of hu37 serotype containing an oversized genome were produced as described in Example 2. Samples were dialyzed into either (A) standard background buffer (40 mM bis-tris propane, 20 mM HEPES, 20 mM citrate, 200 mM NaCl, (w/v) Pluronic F68, pH 8.0), standard background buffer containing (B) 0.1 mM $MgCl_2$, (C) 10 mM $MgCl_2$, (D) 25 mM $MgCl_2$, (E) 50 mM $MgCl_2$, (F) 100 mM $MgCl_2$, or (G) 200 mM $MgCl_2$. Samples were heated to the temperatures and for the durations shown in Table 1. Genomic integrity of AAV particles was measured by DRP-qPCR. Results of the experiment are presented in Table 2. Residual titer was determined by comparing against a starting sample which was not exposed to elevated temperatures and kept at 4° C. and is reported as a percentage. The coefficient of variation (% CV) is also reported.

Figure 6:
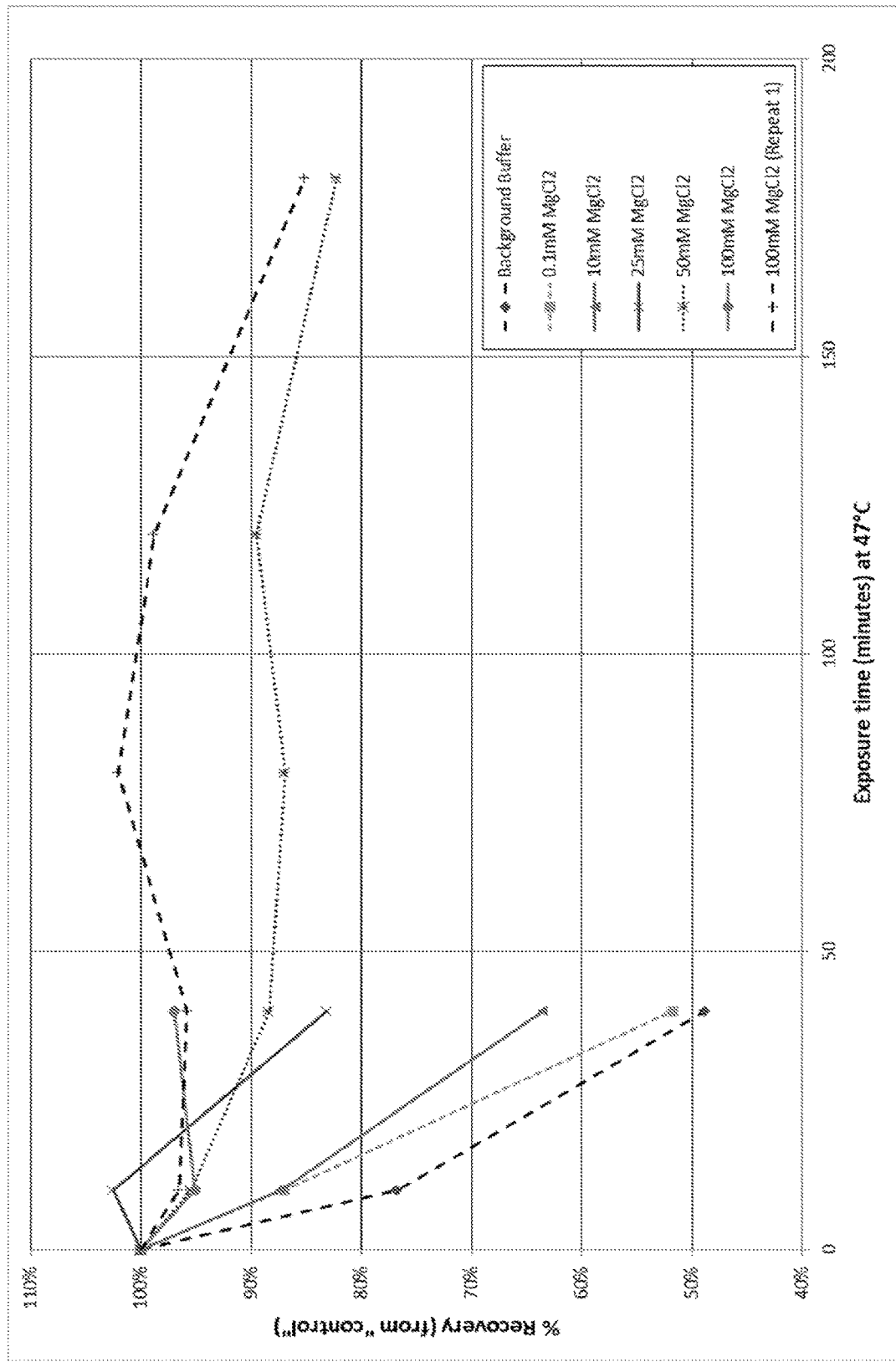
FIG. 6 depicts a comparison of the percentage recovery for a HEK293-produced, hu37 serotype, oversized AAV vector in seven different buffers as a function of time of exposure to 47° C. Either a background buffer of 40 mM bis-tris propane, 20 mM HEPES, 20 mM citrate, 200 mM NaCl, 0.001% (w/v) Pluronic F68, pH 8.0, was used, or background buffer supplemented with 0.1 mM, 10 mM, 25 mM, 50 mM, or 100 mM $MgCl_2$. A DRP-qPCR assay was used to determine levels of AAV product pre- and post-exposure. The "control" was a load sample which remained frozen for the entire experiment.

FIG. 6 shows the recovery of AAV vectors in buffer containing from 0 to 100 mM $MgCl_2$ at 47° C., over 40 minutes. Samples in buffer containing less than 25 mM $MgCl_2$ had significantly lower recovery at all time points.

Figure 7:
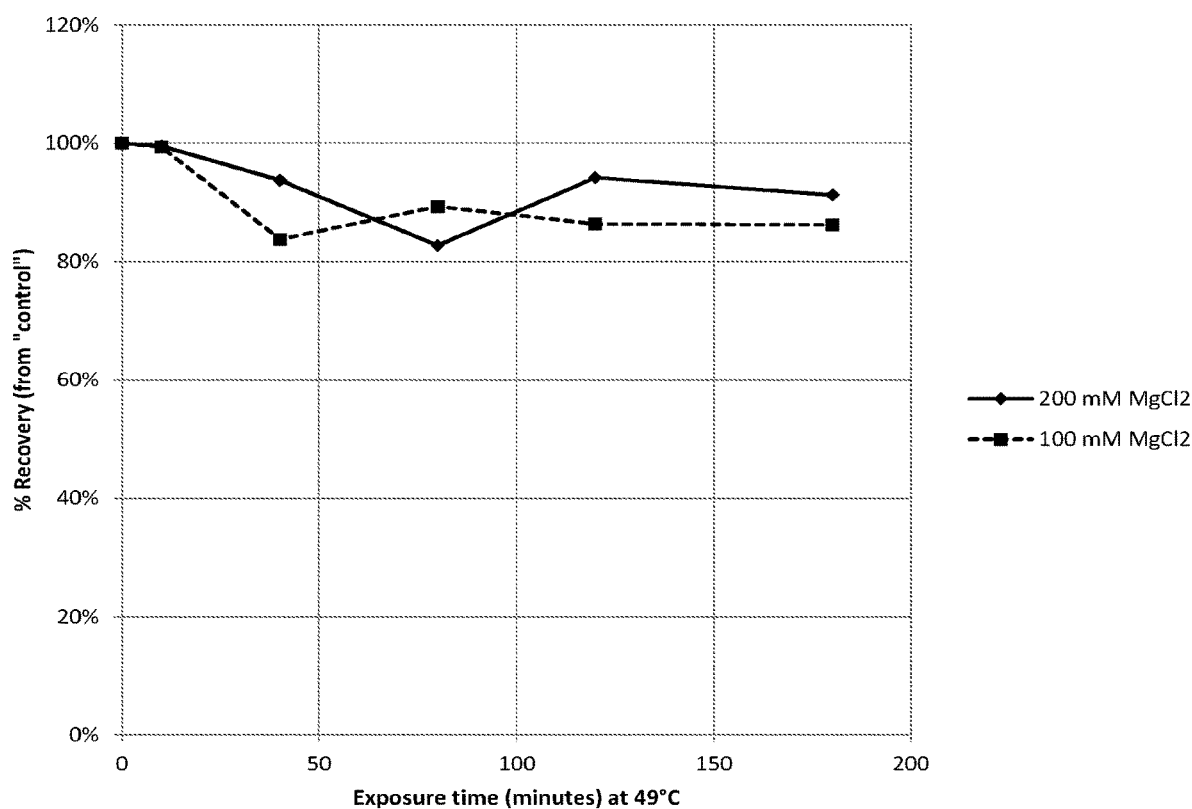
FIG. 7 depicts a comparison of the percentage recovery for a HEK293-produced, hu37 serotype, oversized AAV vector in two different buffers as a function of time of exposure to 49° C. Either a background buffer of 40 mM bis-tris propane, 20 mM HEPES, 20 mM citrate, 200 mM NaCl, 0.001% (w/v) Pluronic F68, pH 8.0, supplemented with 100 mM or 200 mM $MgCl_2$ was used. A DRP-qPCR assay was used to determine levels of AAV product pre- and post-exposure. The "control" was a load sample which remained frozen for the entire experiment.
Figure 8:
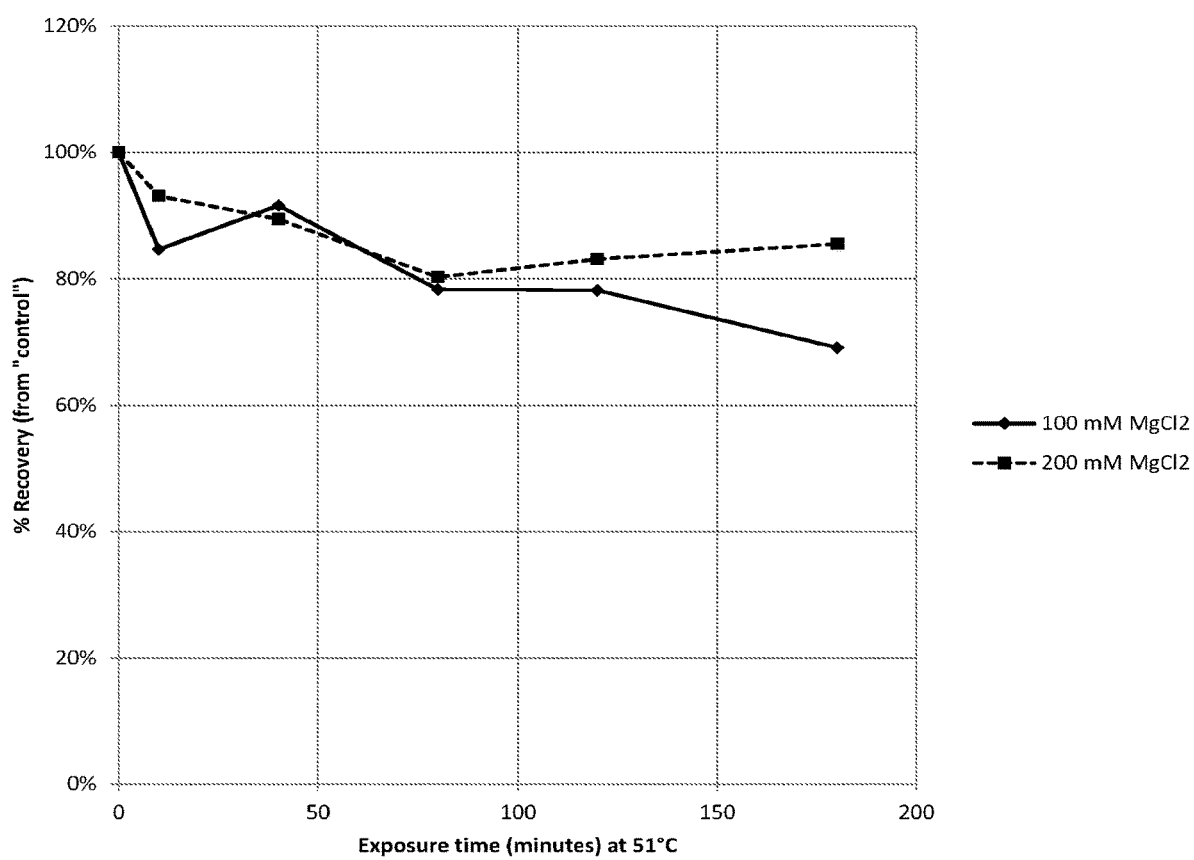
FIG. 8 depicts a comparison of the percentage recovery for a HEK293-produced, hu37 serotype, oversized AAV vector in two different buffers as a function of time of exposure to 51° C. Either a background buffer of 40 mM bis-tris propane, 20 mM HEPES, 20 mM citrate, 200 mM NaCl, 0.001% (w/v) Pluronic F68, pH 8.0, supplemented with 100 mM or 200 mM $MgCl_2$ was used. A DRP-qPCR assay was used to determine levels of AAV product pre- and post-exposure. The "control" was a load sample which remained frozen for the entire experiment.
Figure 9:
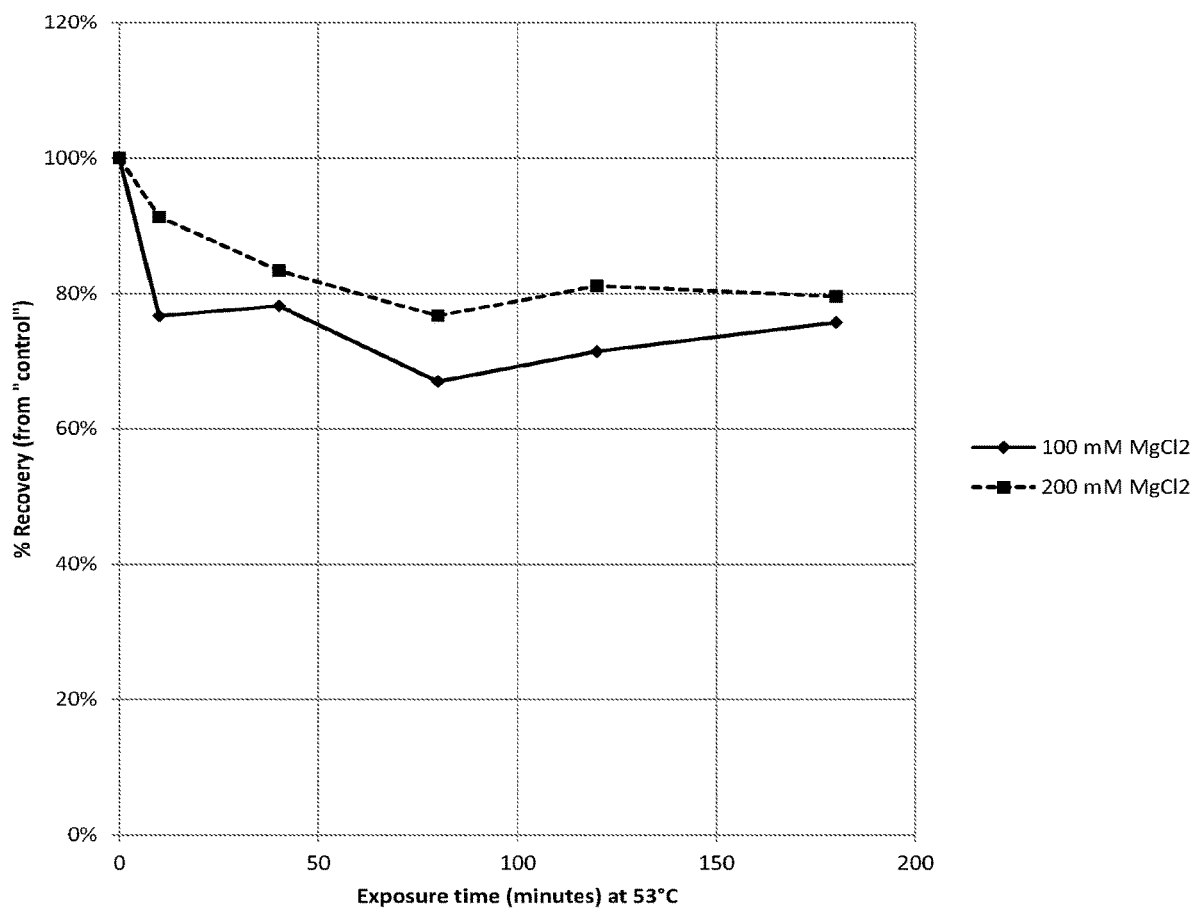
FIG. 9 depicts a comparison of the percentage recovery for a HEK293-produced, hu37 serotype, oversized AAV vector in two different buffers as a function of time of exposure to 53° C. Either a background buffer of 40 mM bis-tris propane, 20 mM HEPES, 20 mM citrate, 200 mM NaCl, 0.001% (w/v) Pluronic F68, pH 8.0, supplemented with 100 mM or 200 mM $MgCl_2$ was used. A DRP-qPCR assay was used to determine levels of AAV product pre- and post-exposure. The "control" was a load sample which remained frozen for the entire experiment.
Figure 10:
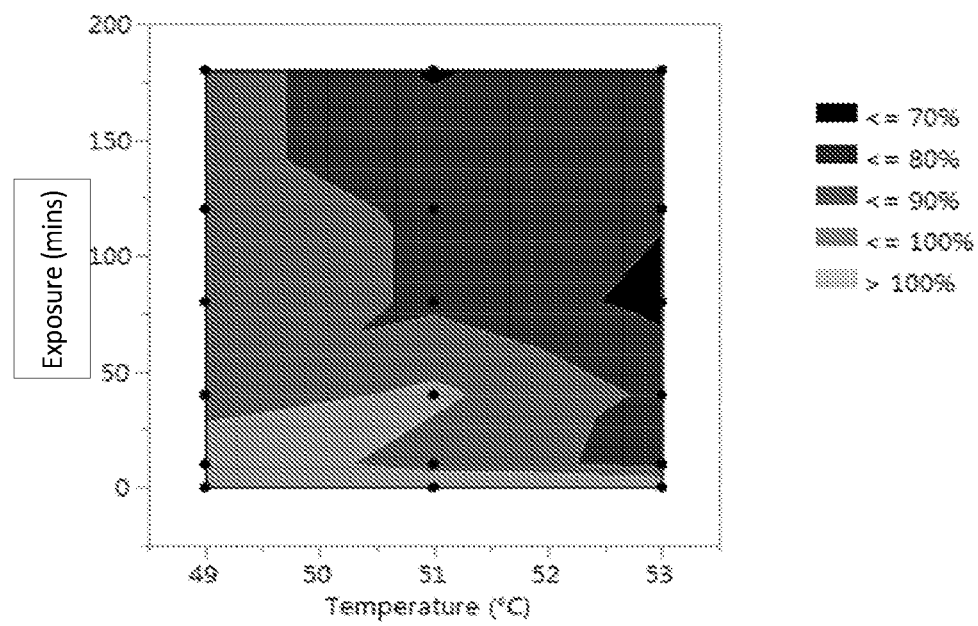
FIG. 10 depicts a contour plot showing the percent yield of HEK293-produced, hu37 serotype, oversized product in a background of 40 mM bis-tris propane, 20 mM HEPES, 20 mM citrate, 200 mM NaCl, 0.001% (w/v) Pluronic F68, pH 8.0, supplemented with 100 mM $MgCl_2$ A DRP-qPCR assay was used to determine levels of AAV product pre- and post-exposure. Actual data points are shown by black dots, with the contour map interpolated between said data points.
Figure 11:
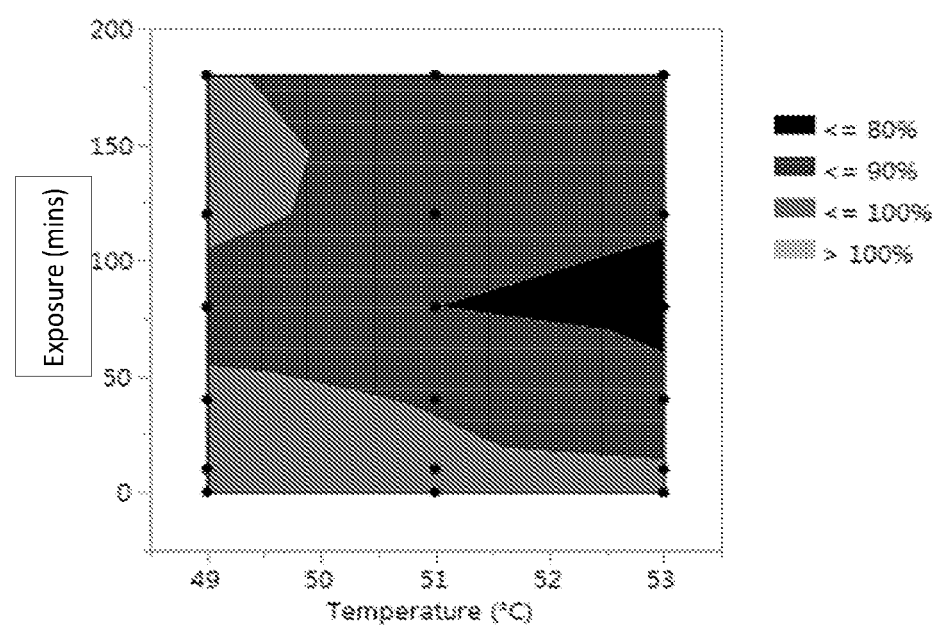
FIG. 11 depicts a contour plot showing the percent yield of HEK293-produced, hu37 serotype, oversized product in a background of 40 mM bis-tris propane, 20 mM HEPES, 20 mM citrate, 200 mM NaCl, 0.001% (w/v) Pluronic F68, pH 8.0, supplemented with 200 mM $MgCl_2$ A DRP-qPCR assay was used to determine levels of AAV product pre- and post-exposure. Actual data points are shown by black dots, with the contour map interpolated between said data points.

FIG. 7 shows the recovery of AAV vectors in buffer containing 100 mM or 200 mM MgCl$_2$ at 49° C. for 180 minutes. FIG. 8 shows the recovery of AAV vectors in buffer containing 100 mM or 200 mM MgCl$_2$ at 51° C. for 180 minutes. FIG. 9 shows the recovery of AAV vectors in buffer containing 100 mM or 200 mM MgCl$_2$ at 53° C. for 180 minutes. Overall, these data suggest that buffer containing 200 mM MgCl$_2$ provides slightly better protection against degradation during extended heating. These differences are depicted in FIGS. 10 and 11, which show slightly increased vector loss with increased duration and temperature for buffer containing 100 mM MgCl$_2$ versus buffer containing 200 mM MgCl$_2$.

TABLE 1

| Buffer formulation | Temp. and duration |
| --- | --- |
| Buffer (A) (control) | 47° C. for 0, 10 or 40 min |
| Buffer (B) (0.1 mM MgCl$_2$) | 47° C. for 0, 10, or 40 min |
| Buffer (C) (10 mM MgCl$_2$) | 47° C. for 0, 10, or 40 min |
| Buffer (D) (25 mM MgCl$_2$) | 47° C. for 0, 10, or 40 min |
| Buffer (E) (50 mM MgCl$_2$) | 47° C. for 0, 10, 40, 80, 120, or 180 min |
| Buffer (F) (100 mM MgCl$_2$) | 47° C. for 0, 10, 40, 80, 120, or 180 min |
| | 49° C. for 0, 10, 40, 80, 120, or 180 min |
| | 51° C. for 0, 10, 40, 80, 120, or 180 min |
| | 53° C. for 0, 10, 40, 80, 120, or 180 min |
| Buffer (G) (200 mM MgCl$_2$) | 49° C. for 0, 10, 40, 80, 120, or 180 min |
| | 51° C. for 0, 10, 40, 80, 120, or 180 min |
| | 53° C. for 0, 10, 40, 80, 120, or 180 min |

TABLE 2

| Buffer formulation | Exposure (mins) | Temp (° C.) | Residual Titer | % CV |
| --- | --- | --- | --- | --- |
| Buffer (A) (control) | 0 | 47 | 100% | 5.2% |
| Buffer (A) (control) | 10 | 47 | 77% | 4.7% |
| Buffer (A) (control) | 40 | 47 | 49% | 14.5% |
| Buffer (B) (0.1 mM MgCl$_2$) | 0 | 47 | 100% | 3.6% |
| Buffer (B) (0.1 mM MgCl$_2$) | 10 | 47 | 87% | 6.3% |
| Buffer (B) (0.1 mM MgCl$_2$) | 40 | 47 | 52% | 2.2% |
| Buffer (C) (10 mM MgCl$_2$) | 0 | 47 | 100% | 8.6% |
| Buffer (C) (10 mM MgCl$_2$) | 10 | 47 | 87% | 1.9% |
| Buffer (C) (10 mM MgCl$_2$) | 40 | 47 | 63% | 5.3% |
| Buffer (D) (25 mM MgCl$_2$) | 0 | 47 | 100% | 3.3% |
| Buffer (D) (25 mM MgCl$_2$) | 10 | 47 | 103% | 3.5% |
| Buffer (D) (25 mM MgCl$_2$) | 40 | 47 | 83% | 10.1% |
| Buffer (E) (50 mM MgCl$_2$) | 0 | 47 | 100% | 1.5% |
| Buffer (E) (50 mM MgCl$_2$) | 10 | 47 | 95% | 3.3% |
| Buffer (E) (50 mM MgCl$_2$) | 40 | 47 | 88% | 4.5% |
| Buffer (E) (50 mM MgCl$_2$) | 80 | 47 | 87% | 4.0% |
| Buffer (E) (50 mM MgCl$_2$) | 120 | 47 | 90% | 2.1% |
| Buffer (E) (50 mM MgCl$_2$) | 180 | 47 | 82% | 3.4% |
| Buffer (F) (100 mM MgCl$_2$) | 0 | 47 | 100% | 8.7% |
| Buffer (F) (100 mM MgCl$_2$) | 0 | 47 | 100% | 2.6% |
| Buffer (F) (100 mM MgCl$_2$) | 10 | 47 | 95% | 5.2% |
| Buffer (F) (100 mM MgCl$_2$) | 10 | 47 | 97% | 1.9% |
| Buffer (F) (100 mM MgCl$_2$) | 40 | 47 | 97% | 6.9% |
| Buffer (F) (100 mM MgCl$_2$) | 40 | 47 | 96% | 3.9% |
| Buffer (F) (100 mM MgCl$_2$) | 80 | 47 | 102% | 6.2% |
| Buffer (F) (100 mM MgCl$_2$) | 120 | 47 | 99% | 4.6% |
| Buffer (F) (100 mM MgCl$_2$) | 180 | 47 | 85% | 9.8% |
| Buffer (F) (100 mM MgCl$_2$) | 0 | 49 | 100% | 5.2% |
| Buffer (F) (100 mM MgCl$_2$) | 10 | 49 | 99% | 1.2% |
| Buffer (F) (100 mM MgCl$_2$) | 40 | 49 | 84% | 3.5% |
| Buffer (F) (100 mM MgCl$_2$) | 80 | 49 | 89% | 1.4% |
| Buffer (F) (100 mM MgCl$_2$) | 120 | 49 | 86% | 4.4% |
| Buffer (F) (100 mM MgCl$_2$) | 180 | 49 | 86% | 5.0% |
| Buffer (F) (100 mM MgCl$_2$) | 0 | 51 | 100% | 4.2% |
| Buffer (F) (100 mM MgCl$_2$) | 10 | 51 | 85% | 2.2% |
| Buffer (F) (100 mM MgCl$_2$) | 40 | 51 | 92% | 3.9% |
| Buffer (F) (100 mM MgCl$_2$) | 80 | 51 | 78% | 2.6% |
| Buffer (F) (100 mM MgCl$_2$) | 120 | 51 | 78% | 3.2% |
| Buffer (F) (100 mM MgCl$_2$) | 180 | 51 | 69% | 0.7% |
| Buffer (F) (100 mM MgCl$_2$) | 0 | 53 | 100% | 2.0% |
| Buffer (F) (100 mM MgCl$_2$) | 10 | 53 | 77% | 2.0% |
| Buffer (F) (100 mM MgCl$_2$) | 40 | 53 | 78% | 9.5% |
| Buffer (F) (100 mM MgCl$_2$) | 80 | 53 | 67% | 2.7% |
| Buffer (F) (100 mM MgCl$_2$) | 120 | 53 | 71% | 4.0% |
| Buffer (F) (100 mM MgCl$_2$) | 180 | 53 | 76% | 3.1% |
| Buffer (G) (200 mM MgCl$_2$) | 0 | 49 | 100% | 8.3% |
| Buffer (G) (200 mM MgCl$_2$) | 10 | 49 | 99% | 1.8% |
| Buffer (G) (200 mM MgCl$_2$) | 40 | 49 | 94% | 4.7% |
| Buffer (G) (200 mM MgCl$_2$) | 80 | 49 | 83% | 8.2% |
| Buffer (G) (200 mM MgCl$_2$) | 120 | 49 | 94% | 3.1% |
| Buffer (G) (200 mM MgCl$_2$) | 180 | 49 | 91% | 7.9% |
| Buffer (G) (200 mM MgCl$_2$) | 0 | 51 | 100% | 13.0% |
| Buffer (G) (200 mM MgCl$_2$) | 10 | 51 | 93% | 3.8% |
| Buffer (G) (200 mM MgCl$_2$) | 40 | 51 | 89% | 1.6% |
| Buffer (G) (200 mM MgCl$_2$) | 80 | 51 | 80% | 12.3% |
| Buffer (G) (200 mM MgCl$_2$) | 120 | 51 | 83% | 1.2% |
| Buffer (G) (200 mM MgCl$_2$) | 180 | 51 | 85% | 4.8% |
| Buffer (G) (200 mM MgCl$_2$) | 0 | 53 | 100% | 12.2% |
| Buffer (G) (200 mM MgCl$_2$) | 10 | 53 | 91% | 3.4% |
| Buffer (G) (200 mM MgCl$_2$) | 40 | 53 | 83% | 0.9% |
| Buffer (G) (200 mM MgCl$_2$) | 80 | 53 | 77% | 11.6% |
| Buffer (G) (200 mM MgCl$_2$) | 120 | 53 | 81% | 2.8% |
| Buffer (G) (200 mM MgCl$_2$) | 180 | 53 | 80% | 2.1% |

EQUIVALENTS

Various modifications of the invention an and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof

What is claimed is:

1. A method of inactivating helper virus in a sample containing helper virus, adeno-associated virus particles, and a buffer comprising a concentration of 25 mM to 500 mM of divalent or trivalent cations, or a concentration of 0.5 M to 0.6 M of kosmotropic salts, wherein the method comprises:
heating the sample to a temperature of 45° C. to 55° C., and maintaining the sample at the temperature for a time period of 1 minute to 6 hours, thereby inactivating helper virus.

2. The method of claim 1, wherein the sample is maintained at the temperature for a time period of 10 to 180 minutes.

3. The method of claim 1, wherein the method results in a log reduction of helper virus of 6.3 or greater.

4. The method of claim 1, wherein the adeno-associated virus particle comprises a genome of approximately or more than 4.7 kb of DNA.

5. The method of claim 1, wherein the buffer further comprises a chaotropic salt.

6. The method of claim 1, wherein the buffer further comprises a polyol selected from the group consisting of: glycerol, propylene glycol, and 1,6-Hexanediol.

7. The method of claim 1, wherein the buffer maintains a pH of 3.0 to 10.0 at temperatures of 4° C. to 70° C.

8. The method of claim 1, wherein the buffer further comprises: 40 mM bis-tris propane, 20 mM HEPES, 20 mM citrate, 200 mM NaCl, and 0.001% (w/v) Pluronic F68.

9. The method of claim 7, wherein the buffer is a Tris buffer, a phosphate buffer, or a triazolamine buffer.

10. The method of claim 1, wherein the helper virus is an adenovirus.

11. The method of claim 10, where the adenovirus is Ad5.

12. The method of claim 1, wherein the concentration of divalent or trivalent cations is 25 mM to 400 mM.

13. The method of claim 1, wherein the buffer-comprises divalent or trivalent cations of a metal selected from the group consisting of: Mg, Ca, Mn, Ni, Zn, Co, Sr, Cu, Cr, Fe, and Sc.

14. The method of claim 13, wherein the cations are selected from the group consisting of: $Mg^{2+}$, $Ca^{2+}$, $Mn^{2+}$, $Ni^{2+}$, $Zn^{2+}$, $Co^{2+}$, $Sr^{2+}$, $Cu^{2+}$ and $Cr^{2+}$.

15. The method of claim 14 wherein the cations are $Ca^{2+}$.

16. The method of claim 14 wherein the cations are $Mg^{2+}$.

17. The method of claim 13, wherein the cations are $Sc^{3+}$.

18. The method of claim 1, wherein the buffer comprises a kosmotropic salt selected from the group consisting of ammonium sulfate, ammonium acetate, sodium citrate, sodium acetate, sodium sulfate, potassium phosphate, and cesium chloride.

19. The method of claim 18, wherein the buffer comprises ammonium sulfate.

20. The method of claim 18, wherein the concentration of kosmotropic salts is 0.5 M.

\* \* \* \* \*